United States Patent [19]

Greene

[11] 4,036,836

[45] July 19, 1977

[54] PROCESS FOR PRODUCING 2-PYRROLIDONE

[75] Inventor: Janice L. Greene, Chagrin Falls, Ohio

[73] Assignee: Standard Oil Company, Cleveland, Ohio

[21] Appl. No.: 591,883

[22] Filed: June 30, 1975

[51] Int. Cl.$^2$ .......................................... C07D 207/26
[52] U.S. Cl. .......................................... 260/326.5 FN
[58] Field of Search .............................. 260/326.5 FN

[56] References Cited

U.S. PATENT DOCUMENTS

| 2,351,939 | 6/1944 | Drossbach | 260/326.5 FN |
| 3,095,423 | 6/1963 | Copenhaver et al. | 260/326.5 FN |
| 3,644,402 | 2/1972 | Takagi et al. | 260/326.5 FN |
| 3,781,298 | 12/1973 | Davis | 260/326.5 FN |
| 3,806,427 | 4/1974 | Gervasi et al. | 260/326.5 FN |

FOREIGN PATENT DOCUMENTS 976,939  12/1964  United Kingdom ....... 260/326.5 FN

OTHER PUBLICATIONS

Freidlin et al.; Chem. Ab., vol. 62, 1162b (1965).
Barnett; Chem Ab., vol. 71, 38227h (1969).

*Primary Examiner*—Donald G. Daus
*Assistant Examiner*—Mary C. Vaughn
*Attorney, Agent, or Firm*—Herbert D. Knudsen; Evelyn R. Kosman

[57] ABSTRACT

A process for producing 2-pyrrolidone which comprises the simultaneous hydrolysis and hydrogenation of succinonitrile at elevated temperatures and pressures in the presence of a hydrogenation catalyst consisting essentially of nickel boride.

5 Claims, No Drawings

PROCESS FOR PRODUCING 2-PYRROLIDONE

This invention relates to a process for the synthesis of 2-pyrrolidone (also known as 2-pyrrolidinone) from succinonitrile. More particularly this invention relates to the synthesis of 2-pyrrolidone by the simultaneous hydrolysis and hydrogenation of succinonitrile at elevated temperatures and pressures in the presence of a hydrogenation catalyst consisting essentially of nickel boride.

BACKGROUND OF THE INVENTION

Pyrrolidone is particularly useful as an intermediate in the preparation of Nylon-4, in the preparation of N-methylpyrrolidone and N-vinylpyrrolidone which are useful as organic solvents, and in the formation of polymers which have certain specific properties.

Pyrrolidone has been prepared according to U.S. Pat. No. 3,095,423 in a liquid phase process comprising the simultaneous hydrogenation and hydrolysis of succinonitrile utilizing aqueous ammonia and hydrogen pressures of at least 500 psi, in the presence of a hydrogenation catalysts such as the oxides of ruthenium, palladium and platinum, Raney nickel and Raney cobalt, and the like. U.S. Pat. No. 3,781,298 also describes a single step process for preparing 2-pyrrolidone by hydrogenating succinonitrile in an aqueous solution in the presence of a Raney cobalt catalyst at pressures greater that 2000 psig. U.S. Pat. No. 3,644,402 discloses a two-step process for hydrolyzing and hydrogenating succinonitrile sequentially, wherein the hydrolysis reaction is conducted in aqueous ammonia and the hydrogenation in the presence of a nitrogen-containing basic organic solvent and a catalyst such as nickel-silica gel, palladium-carbon, Raney nickel, Raney cobalt, and the like, at pressures of from about 750 to 3000 psi. None of the processes of the prior art, however, teach the use of nickel boride as the hydrogenation catalyst as employed in the instant invention.

SUMMARY OF THE INVENTION

According to the present invention, it has been discovered that improved yields of 2-pyrrolidone can be obtained by contacting an aqueous mixture of succinonitrile with hydrogen at elevated temperatures and pressures in the presence of a hydrogenation catalyst consisting essentially of nickel boride. The overall reaction taking place in this process may be represented by the following equation:

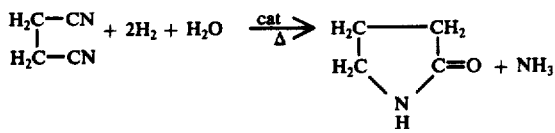

Although various forms of nickel catalysts, and in particular Raney nickel are frequently employed in processes for the conversion of succinonitrile to 2-pyrrolidone, it is surprising that substantially higher conversions are obtained with the use of nickel boride as a catalyst.

THE CATALYST

The nickel boride catalyst employed in this invention may be prepared by various methods known to those skilled in the art. However, it may be conveniently prepared by co-reacting a nickel salt and a borohydride salt in a dilute aqueous solution. The conditions under which the catalyst components are mixed are not critical, and satisfactory results are obtained by mixing the components at room temperature. When bubbling has ceased, the black nickel boride precipitate can be separated from the aqueous phase by various means such as by decantation or filtration under a nitrogen atmosphere. The nickel boride precipitate is then washed with water and either used immediately or stored under water.

Any one of numerous nickel salts may be employed in the preparation of the nickel boride, and nickel salts such as the acetate, halide, nitrate, sulfate, carboxylate, and the like, have been found to give satisfactory results. The preferred nickel salt is nickel acetate, however. The borohydride salt may be a metal borohydride or a quaternary ammonium borohydride such as, for example, tetraethyl ammonium borohydride, which is most readily avilable. Preferably, for reasons of availability, the cation of the borohydride is an alkali metal, and more preferably sodium or potassium.

Aqueous solutions of the nickel salt and the borohydride salt are conveniently mixed at room temperature, although mixing may take place at temperatures from about 0° up to about 60° C. The molar ratio of the catalyst components employed may vary over a wide range, and molar ratios of the borohydride salt to nickel salt of from about 1:1 to 12:1 are feasible.

The nickel boride catalyst can be employed in an unsupported form or in a supported form wherein the support or carrier may consist of an inert material such as carbon, alumina, silica, silica-alumina, kieselguhr, or other well-known supports. The support may be employed in amounts of from about 1 to 95% by weight of the total catalyst composition.

THE PROCESS

In carrying out the process of the present invention the amount of nickel boride catalyst used in the reaction may vary widely, and normally from 0.1 to 40 percent by weight is used, based on the weight of succinonitrile employed in the reaction. However, it is more preferable to use from about 3.5 to 35 weight percent catalyst based on the weight of the succinonitrile employed. The catalyst may be conveniently recovered from the reaction mixture by filtration or decantation, and it can be reused in subsequent reactions, normally without regeneration.

The ratio of the reactants charged to the reactor in the process of this invention are not critical. Water can be present in stoichiometric amounts, i.e., one mole of water/mole of succinonitrile, or excess water may be used. Generally, it is preferred to employ from about 5-25 moles of water per mole of succinonitrile. The upper limit of the amount of water used is governed by the excessive hydrolysis of succinonitrile to succinimide and by the economics of product recovery, and the lower limit is governed by polymer formation.

While the reaction may be carried out using hydrogen pressures ranging from about 100 to about 1500 psi, one of the more important advantages associated with this process is that optimum results are obtained at much lower hydrogen pressures than are employed in processes of the prior art. The use of lower hydrogen pressures tends to minimize the excessive hydrogenation of succinonitrile to pyrrolidine and related products, and the use of lower pressures has an important economic significance particularly in relation to the need for less expensive reactor equipment. Preferably hydrogen pressures of from about 300 to 750 psi are utilized.

A reaction promoter may be advantageously included in the reaction if so desired, and such promoters as 2-pyrrolidone or an N-alkyl-2-pyrrlidone wherein the alkyl group may contain from 1 to 6 carbon atoms may be employed. When utilized, beneficial results are readily obtained with reaction promoters employed in concentrations ranging from about 0.1 to 1.5 moles per mole of succinonitrile.

The reaction of this invention may be conducted by means of various techniques, and both batch-type and continuous operations are contemplated. Further benefits are realized by recycling the reaction product to the reaction mixture. In carrying out the process, water, succinonitrile, the promoter and the catalyst are charged to a reactor in the desired concentrations, and the reactor is then closed and further charged with hydrogen. The temperatures of the reaction mixture is then raised to the level desired, with stirring. The reaction temperature may range from about 50° to 300° C but preferably temperatures within the range of from about 100° to 200° C are employed. The reaction is continued at the desired temperature for from about 0.5 to 6 hours, but with continuous operation, contact times may be as low as 0.1 hours. Preferably the reaction time is within the range of from about 2 to 5 hours, after which time the heat is removed, and the reaction mass is allowed to cool. The reaction mixture is then filtered to remove the catalyst and flash distilled to remove excess water and volatile components. The product, 2-pyrrolidone, is then recovered in good yields by fractional distillation of the remaining reaction mixture.

SPECIFIC EMBODIMENTS

CATALYST PREPARATION

CATALYST (A)

An aqueous solution containing 0.3 mole of sodium borohydride ($NaBH_4$) was slowly added over a period of 0.5 hours in 3 portions to a stirred aqueous solution containing 0.1 mole nickel acetate [$Ni(C_2H_3O_2)_2$] at room temperature. When the bubbling had ceased, the black precipitate was allowed to settle and the aqueous phase decanted. The precipitate was washed three times with distilled water to give 6.4 grams of catalyst which was subsequently stored under water.

precipitate of the nickel boride was separated from the aqueous phase by filtration under a nitrogen atmosphere. The precipitate was washed three times with distilled water that was heated to 60° C, and 6.4 grams of catalyst were obtained. The catalyst was subsequently stored under water until used.

Comparative Examples A & B and Examples 1-3

The reaction in each example was carried out by placing deionized water, succinonitrile and a hydrogenation catalyst in a one-liter, stainless steel Parr autoclave. The autoclave was flushed with nitrogen for 5 minutes, and with stirring was pressured to 200 psig. with nitrogen and checked for leakage by increasing the nitrogen pressure to twice that of the working pressure for a period of 15 minutes. When no leaks were detected the nitrogen was vented, the autoclave heated to 60° for a half hour, then pressured with hydrogen to the working pressure. As hydrogen was consumed, hydrogen was added from time to time to maintain the working pressure. Stirring and heating were continued for about one hour after the hydrogen addition and before the reaction temperature of 140° C was reached. The exothermic reaction often carried the reaction to a slightly higher temperature as indicated in Table 1. Periodically, samples were removed from the autoclave and were analyzed by gas-liquid chromatography for unreacted succinonitrile, pyrrolidone and the hydrolysis products, succinimide and succinic acid. The conditions under which the maximum pyrrolidone conversion was observed were then recorded. At that time the succinonitrile conversion was usually complete. Other by-products identified in addition to succinimide and succinic acid were pyrrolidine and butyrolactone. The reaction contents were then cooled, filtered, and concentrated by means of vacuum stripping.

In comparative examples A and B, the hydrogenation catalysts utilized were a supported nickel catalyst on a kieselguhr support and a Raney nickel cayalyst, both of which are representative of catalysts employed in the prior art. In examples 1, 2 & 3 which represent the present invention, the hydrogenation catalyst employed was nickel boride.

Examples 1, 2 and 3 summarized in Table 1 show the superiority of nickel boride catalyst for the conversion of succinonitrile to 2-pyrrolidone as compared with the nickel catalysts of the prior art shown in comparative examples A and B.

Table 1

| | | Effect of Catalyst Composition on the Conversion of Succinonitrile to 2-Pyrrolidone | | | | | |
|---|---|---|---|---|---|---|---|
| | | Reactant Ratios | | Reaction Conditions | | | Net % Conversion |
| Example | Catalyst | Grams of Catalyst/ Mole SN | Moles $H_2O$/ Mole SN | $H_2$ Press. (psig.) | Reaction Temp. ° C | Reaction Time. Hrs. | of Succinonitrile to 2-Pyrrolidone |
| Comp. A | 60% Nickel/ 40% Kieselguhr | 25 | 20 | 450 | 139 | 4.4 | 37.8 |
| Comp. B | Raney Nickel | 25 | 20 | 450 | 145 | 4.0 | 31 |
| 1 | Nickel boride(A) | 3 | 20 | 450 | 138 | 5.2 | 49.5 |
| 2 | Nickel boride(B) | 12.25 | 20 | 450 | 140 | 4.3 | 46.1 |
| 3 | *Nickel boride(A) | 3 | 20 | 450 | 139 | 6.0 | 59.5 |

*0.5 moles of the promoter, 2-pyrrolidone, per mole of succinonitrile was added to the reaction mixture.

CATALYST (B)

An aqueous solution containing 0.6 moles of sodium borohydride ($NaBH_4$) was slowly added over a period of 0.5 hours in 3 portions to a stirred aqueous solution of 0.1 mole of nickel chloride ($NiCl_2$) at a temperature from 0°–≈° C. The mixture was digested for a period of time at 60° C. When the bubbling ceased, the black

I claim:

1. In the process for the preparation of 2-pyrrolidone by contacting an aqueous mixture of succinonitrile with hydrogen at elevated temperatures and pressures in the presence of a hydrogenation catalyst, the improvement comprising employing a hydrogenation catalyst consisting essentially of nickel boride.

2. The process in claim 1 wherein the nickel boride catalyst is employed within the concentration range of from about 0.1 to 40 percent by weight, based on the weight of succinonitrile employed.

3. The process in claim 1 wherein the nickel boride catalyst is on an inert support.

4. The process in claim 2 wherein the hydrogen pressures is in the range of from about 100 to 1500 psi.

5. The process in claim 4 wherein the reaction temperature is in the range of from 50° to 300° C.

* * * * *